United States Patent [19]

Thomas

[11] 4,226,745
[45] Oct. 7, 1980

[54] CIS-10,10-DIMETHYL-TRICYCLO[7.1.1.0$^{2,7}$]UNDEC-2-EN-4-ONE AS PERFUMING INGREDIENT

[75] Inventor: Alan F. Thomas, Nyon, Switzerland

[73] Assignee: Firmenich, S.A., Geneva, Switzerland

[21] Appl. No.: 969,583

[22] Filed: Dec. 14, 1978

[30] Foreign Application Priority Data

Jan. 13, 1978 [CH] Switzerland .......................... 360/78

[51] Int. Cl.$^2$ ............................................. C11B 9/00
[52] U.S. Cl. .................................. 252/522 R; 260/398; 426/538; 252/108; 252/305; 252/89.1; 131/17 R; 131/144; 568/373
[58] Field of Search ....................... 252/522; 260/586

[56] References Cited

U.S. PATENT DOCUMENTS

| | | | |
|---|---|---|---|
| 4,124,642 | 11/1978 | Buchi et al. | 252/522 R |
| 4,142,997 | 3/1979 | Maurer | 252/522 R |

OTHER PUBLICATIONS

A. van der Gen et al., Receueil Trav. Chim. Pays–Bas 90, pp. 1034–1044, and 1045–1054, 1971.

*Primary Examiner*—Veronica O'Keefe
*Attorney, Agent, or Firm*—Scully, Scott, Murphy & Presser

[57] ABSTRACT

New tricyclic carbonyl derivative, viz. cis-10,10-dimethyl-tricyclo[7.1.1.0$^{2,7}$]undec-2-en-4-one, and its use as flavoring and perfuming material.

2 Claims, No Drawings

CIS-10,10-DIMETHYL-TRICYCLO[7.1.1.0²,⁷]UNDEC-2-EN-4-ONE AS PERFUMING INGREDIENT

SUMMARY OF THE INVENTION

The present invention relates to a new tricyclic carbonyl derivative of formula

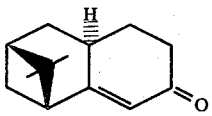

also defined as cis-10,10-dimethyl-tricyclo[7.1.1.0$^{2,7}$]undec-2-en-4-one.

This invention provides a method for improving, enhancing or modifying the organoleptic properties of perfumes and perfumed products as well as of foodstuffs, beverages, pharmaceutical preparations and tobacco products, which method comprises adding thereto a perfuming or flavouring effective amount of cis-10,10-dimethyl-tricyclo[7.1.1.0$^{2,7}$]undec-2-en-4-one.

This invention relates further to a perfuming and a flavouring composition which comprises having added thereto cis-10,10-dimethyl-tricyclo[7.1.1.0$^{2,7}$]undec-2-en-4-one together with another perfuming ingredient, a carrier or a diluent.

Finally the present invention relates to a perfume, a perfume base or a perfumed product as well as a foodstuff, a beverage, a pharmaceutical preparation or a tobacco product which comprises having added thereto cis-10,10-dimethyl-tricyclo[7.1.1.0$^{2,7}$]undec-2-en-4-one.

BACKGROUND OF THE INVENTION

In the course of an investigation on the synthesis of optically active eremophilane sesquiterpenoids from sabinene, A. van der Gen et al. [Rec. Trav. Chim. Pays-Bas, 90, 1034 (1971)] synthesized a compound to which they attributed the structure of trans-10,10-dimethyl-tricyclo[7.1.1.0$^{2,7}$]undec-2-en-4-one. No indication as to the properties of this ketone was however given by the cited authors, nor any suggestion was formulated by them concerning its possible use as perfume or flavour ingredient. We have now found that cis-10,10-dimethyl-tricyclo[7.1.1.0$^{2,7}$]undec-2-en-4-one possesses useful organoleptic properties and consequently it can advantageously be used in the perfume and flavour industry.

PREFERRED EMBODIMENTS OF THE INVENTION

Cis-10,10-dimethyl-tricyclo[7.1.1.0$^{2,7}$]undec-2-en-4-one (I) is a novel compound which can be synthesized starting from nopinone according to the method illustrated hereinafter;

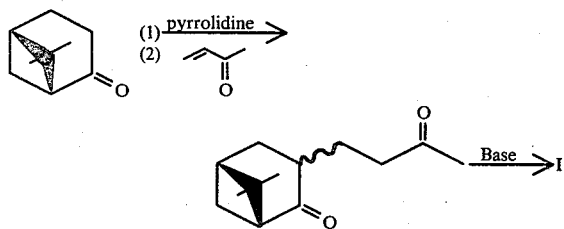

The first step of the above mentioned method consists in reacting nopinone with pyrrolidine in the presence of an acidic dehydrating agent in order to obtain the corresponding enamine [see e.g.: J. Amer. Chem. Soc., 85, 207(1963)]. The thus obtained enamine is then reacted with but-1-en-3-one under the conditions of the so-called Michael reaction to give 3-(3-oxobutyl)-6,6-dimethyl-norpinan-2-one and this latter intermediate is finally reacted with a strong base, e.g. an alkali metal hydroxide in an aqueous alcoholic medium, to yield desired compound (I).

Nopinone, used as starting material in the above mentioned process, can readily be obtained from β-pinene, e.g. in accordance with the procedure described in Rec. Trav. Chim. Pays-Bas 90, 1034 (1971).

In the field of perfumery, compound (I) is characterized by its original scent possessing tobacco, hay, honey and spicy notes reminiscent of certain aspects of the odour of tonka beans. The compound of the invention is consequently very appreciated for the reproduction of fragrance notes of tobacco, spicy, musky, amber or even vanilla types to which it confers fineness and harmony.

Cis-10,10-dimethyl-tricyclo[7.1.1.0$^{2,7}$]undec-2-en-4-one can be advantageously used in both fine and technical perfumery. The proportions at which the compound in question can produce interesting olfactive effects can vary within wide limits. In a given composition, compound (I) can be used in proportions of between about 1 and 25% by weight based on the total weight of the composition to which it has been incorporated. Concentrations lower than the above indicated limits can be used in the perfuming of technical products such as soaps, shampoos, cosmetics or household materials.

In the field of flavours, compound (I) is characterized by a taste and aroma of sweet, tobacco, green, hay and herbaceous character, reminiscent of certain aspects of the odour presented by coumarine. Particularly, the compound of the invention enables the reproduction of the typical top fragrance notes of coumarine in foodstuffs, beverages and tobacco for example.

Cis-10,10-dimethyl-tricyclo[7.1.1.0$^{2,7}$]undec-2-en-4-one can be advantageously used as flavouring ingredient in the manufacture of flavour compositions of varied nature, for instance in butter, nut, caramel or coco flavours. It can be utilized for the aromatization of foodstuffs such as bakery or confectionary products, dairy products, syrups or jellies, pharmaceutical preparations, tobacco and tobacco products.

In the field of flavours, cis-10,10-dimethyl-tricyclo[7.1.1.0$^{2,7}$]undec-2-en-4-one can be used at concentrations of between about 1 and 1000 ppm (parts per million) by weight based on the total weight of the material to be flavoured. Typically, concentrations of between about 10 and 100 ppm achieve the preferred results.

The preparation of the compound of the invention is described hereinbelow in a detailed manner;

cis-10,10-dimethyl-tricyclo[7.1.1.0$^{2,7}$]undec-2-en-4-one (a) A solution of 30 g of nopinone ([α]$_D^{20}$=+39.90; c=8 in ethanol), 29 g of pyrrolidine and 0.4 g of p-toluenesulfonic acid in 150 ml anhydrous benzene was heated at reflux for 40 h under nitrogen atmosphere in a vessel fitted with a water separator. After evaporation of the solvent and distillation of the residue, there were obtained 39.5 g (95% yield) of 1-(6,6-dimethyl-norpin-2-en-2-yl)-pyrrolidine having b.p. 117°–118° C./10 Torr.

NMR: 0.90 (3H, s); 1.34 (1H); 1.38 (3H, s); 2.97 (4H); 4.07 (1H, broad s) δ ppm

MS : M+ =191 (47); m/e =123 (100), 122 (57), 95 (65), 70 (48), 41 (59).

(b) A solution of 39.4 g of the product obtained in accordance with letter (a) above and 14.4 g of but-1-en-3-one in 100 ml of anhydrous dioxane, was stirred for 2 h at room temperature. After addition thereto of 250 ml of a 10% aqueous solution of $Na_2CO_3$, stirring was carried on for about 5 more hours whereupon the mixture was extracted with ether.

Evaporation of the volatile parts followed by distillation of the residue enabled to obtain 35.5 g (yield 82%) of 3-(3-oxo-butyl)-6,6-dimethyl-norpinan-2-one having b.p. 110° C./10 Torr.

NMR: 0.68 and 0.82 (3H, 2s); 1.31 (3H, s); 2.05 (3H, s) δ ppm

IR: 1705, 1662 cm$^{-1}$

MS : M+ =208 (5); me/e=150 (21), 107 (55), 95 (76), 83 (100), 81 (28), 69 (28), 55 (49), 41 (45).

(c) 3 g of the product obtained sub letter (b) above in admixture with an excess of a 45% solution of KOH in water and methanol, were first refluxed during 2 h, then diluted with water and finally extracted with chloroform. The organic extracts were washed with water, dried over Mg SO$_4$ and fractionally distilled to give a b.p. 88°–90° C./0.01 Torr cis-10,10-dimethyl-tricyclo[7.1.1.0$^{2,7}$]undec-2-en-4-one. $d_4^{20}$=1.0152; $[\alpha]_D^{20}$=+40.4° (pure liquid)

Cis-10,10-dimethyl-tricyclo[7.1.1.0$^{2,7}$]undec-2-en-4-one can be more readily obtained as follows: 25.6 g of but-1-en-3-one in 30 ml of anhydrous dioxane were added to a solution of 55.3 g of the product obtained sub letter (a) in 30 ml of dioxane. Immediately after the mixing of reactants the temperature of the reaction mixture raised to 40° C. and decreased then during 1 h to 25° C. 107 ml of a 45% solution of KOH in water and 615 ml of methanol were added to the mixture which was refluxed during 6 h.

After evaporation of the excess of methanol and dilution with water, the reaction mixture was extracted with chloroform and the procedure was continued in accordance with letter (c) above. 37 g of the desired product were thus isolated.

EXAMPLE 1

2 g of cis-10,10-dimethyl-tricyclo[7.1.1.0$^{2,7}$]undec-2-en-4-one have been incorporated into 100 g of commercial soap paste. The thus perfumed paste was used to manufacture toilet soap bars according to usual techniques and the finished products were submitted to an olfactive evaluation. Their fragrance was judged as being an agreeable, hay-like and spicy one.

EXAMPLE 2

5 g of cis-10,10-dimethyl-tricyclo[7.1.1.0$^{2,7}$]undec-2-en-4-one were added to 95 g of a base composition for Eau de Cologne prepared by mixing together the following ingredients (parts by weight):

| | |
|---|---|
| Lemon oil | 250 |
| Bergamot oil | 300 |
| Orange oil | 150 |
| Petitgrain Bigarade | 100 |
| Neroli Bigarade | 20 |
| Lavendel oil | 70 |
| White thyme | 10 |

The thus obtained base composition once upon dilution at 3% in 95% ethanol gave an Eau de Cologne possessing a warm, spicy and amber-like fragrance.

EXAMPLE 3

A base perfume composition of "Tobacco fancy" type was prepared by admixing the following ingredients (parts by weight):

| | |
|---|---|
| Bergamot oil | 100 |
| Californian lemon oil | 30 |
| Geranium Bourbon oil | 10 |
| Vetiver Bourbon oil | 15 |
| Patchouli oil | 15 |
| Mandarine petitgrain oil | 5 |
| Petitgrain bigarade | 5 |
| Clary sage oil | 10 |
| Oriental sandel wood oil | 20 |
| Synthetic bulgarian rose oil | 10 |
| Orange flower leaf water absolute 10%* | 25 |
| Lavendel absolute | 15 |
| Yugoslavian oak-moss absolute 10%* | 80 |
| Clove oil absolute | 20 |
| Synthetic jasmine absolute | 30 |
| Musk ambrette | 10 |
| Musk ketone | 40 |
| Pentadecanolide | 30 |
| Thujopsanone | 10 |
| Hexyl salicylate | 20 |
| Amyl salicylate | 20 |
| Benzyl salicylate | 30 |
| Benzyl benzoate | 20 |
| Isobutyl benzoate | 10 |
| 4-Isopropyl-cyclohexyl-methanol[1] | 10 |
| Methyl cyclopentylidene-acetate[2] 10%* | 20 |
| Gaiol acetate | 20 |
| Mixture of methyl-ionones[3] | 40 |
| 1,7,7-Trimethyl-decalyl-(3) acetate 10%* | 15 |
| Muscone | 5 |
| Civettone 10%* | 25 |
| Methyl-nonyl acetaldehyde 10%* | 10 |
| Galbanum resinoid | 5 |
| | 730 |

*in diethylphthalate
[1] see e.g. British Patent No. 1,416,658
[2] see DE-OS No. 27 29 121
[3] IRALIA ® (Firmenich SA, Geneva)
[4] see Swiss Patent No. 511,935

The above perfume base is characterized by the absence of ingredients of spicy and coumarinic ingredients such as coumarine, eugenol, heliotropine, hay oil absolute or tobacco absolute, which ingredients are characteristic of the "tobacco" note.

By adding to 73 g of the said base, 7 g of cis-10,10,-dimethyl-tricyclo[7.1.1.0$^{2,7}$]undec-2-en-4-one there was obtained a novel composition which possessed a warm, spicy and "tobacco" fragrance character, which character was not shown by the base.

EXAMPLE 4

A preparation for fondant of praline type was prepared by mixing together the following ingredients (parts by weight):

| | |
|---|---|
| natural praline | 100.00 |
| vegetable fat (m.p. 34° C.) | 40.00 |
| skimmed milk powder | 20.00 |
| glazing sugar | 140.00 |

| | |
|---|---|
| lecithine | 1.00 |
| antioxydant | 0.10 |

To a portion of the thus prepared composition there were added 15 ppm of cis-10,10-dimethyl-tricyclo[7.1.1.0$^{2,7}$]undec-2-en-4-one and the flavoured foodstuff was subjected to the evaluation of a panel of experts. The flavoured foodstuff when compared with the unflavoured one was found to possess a sweet, herbaceous and caramel-like gustative note reminiscent of the typical top-notes of coumarine. Moreover, the aroma perceived was accompanied by a fruity, nutty aftertaste.

EXAMPLE 5

A paste for biscuits manufacture was obtained by mixing together the following ingredients:

| | |
|---|---|
| vegetable margarine | 100 g |
| sodium chloride | 1.5 g |
| wheaten flour | 100 g |
| sugar powder | 100 g |
| eggs | 2 |

To a portion of the above prepared paste there were added 15 ppm of cis-10,10-dimethyl-tricyclo[7.1.1.0$^{2,7}$]undec-2-en-4-one and the thus flavoured foodstuff together with an unflavoured portion of it were heated at 180° C. during 40 minutes.

The obtained biscuits were subjected to an organoleptic evaluation by a panel of experts who declared that those biscuits prepared by means of the flavoured paste possessed a sweeter and more "buttery-lactonic" taste and aroma than those prepared by means of the unflavoured paste. They showed moreover a slightly fruity, coconut gustative note.

EXAMPLE 6

10 g of a 0.1% solution of cis-10,10-dimethyl-tricyclo[7.1.1.0$^{2,7}$]undec-2-en-4-one in 95% ethanol were sprayed onto 100 g of a mixture of tobacco of "american blend" type. The tobacco thus flavoured was used to manufacture "test" cigarettes which were then subjected to organoleptic evaluation by comparison with non-flavoured cigarettes ("control"). The tobacco used to manufacture the control cigarettes was preliminary treated with 95% ethanol. The panel of experts declared that:

1. the smell of the non-smoked flavoured tobacco possessed a herbal note and a stronger odour typical of natural tobacco.
2. the smoke of the "test" cigarettes produced a more pronounced sweet, herbal and coumarine odour than that of the "control" cigarettes.

What I claim is:

1. Method for improving, enhancing or modifying the organoleptic properties of a perfume composition which comprises adding thereto a perfuming effective amount of cis-10,10- dimethyl-tricyclo[7.1.1.0$^{2,7}$]undec-2-en-4-one.

2. A perfume composition which comprises having added thereto cis-10,10-dimethyl-tricyclo-[7.1.1.0$^{2,7}$]undec-2-en-4-one together with at least one other perfuming ingredient, or a diluent.

* * * * *